United States Patent [19]

Johnson

[11] 4,212,301
[45] Jul. 15, 1980

[54] DIGITAL TAMPON

[75] Inventor: Russell L. Johnson, Weyauwega, Wis.

[73] Assignee: Kimberly-Clark Corporation, Neenah, Wis.

[21] Appl. No.: 933,165

[22] Filed: Aug. 14, 1978

[51] Int. Cl.$^2$ ............................................. A61F 13/20
[52] U.S. Cl. .................................................... 128/285
[58] Field of Search ................. 128/263, 270, 285, 296

[56] References Cited

U.S. PATENT DOCUMENTS

| | | | |
|---|---|---|---|
| 3,572,341 | 3/1971 | Glassman | 128/285 |
| 3,857,395 | 12/1974 | Johnson et al. | 128/285 |
| 3,881,485 | 5/1975 | Davis, Jr. | 128/270 |
| 3,981,305 | 9/1976 | Ring | 128/285 |
| 4,010,751 | 3/1977 | Ring | 128/285 |
| 4,018,225 | 4/1977 | Elmi | 128/285 |
| 4,027,673 | 6/1977 | Poncy et al. | 128/285 |
| 4,041,948 | 8/1977 | Flam et al. | 128/285 |

Primary Examiner—Robert W. Michell
Assistant Examiner—C. F. Rosenbaum
Attorney, Agent, or Firm—William D. Herrick; Howard Olevsky

[57] ABSTRACT

A digital tampon of unitary construction made of absorbent material capable of being compressed to self-sustaining form. A portion of the material is compressed to a rod-like shape to provide a rigid central support for the remaining relatively uncompressed portion which originates at the top of the rigid central support and is draped downwardly to surround and extend past the lower terminus of the support to form a finger receiving pocket at the tampon base. During insertion the rigid central rod provides positive support to the softer outer portion, while the portion of the tampon surrounding the finger protects the finger from contact with menstrual fluid. After insertion the finger can easily spread the draped over portion to better deploy and position the tampon within the body.

15 Claims, 31 Drawing Figures

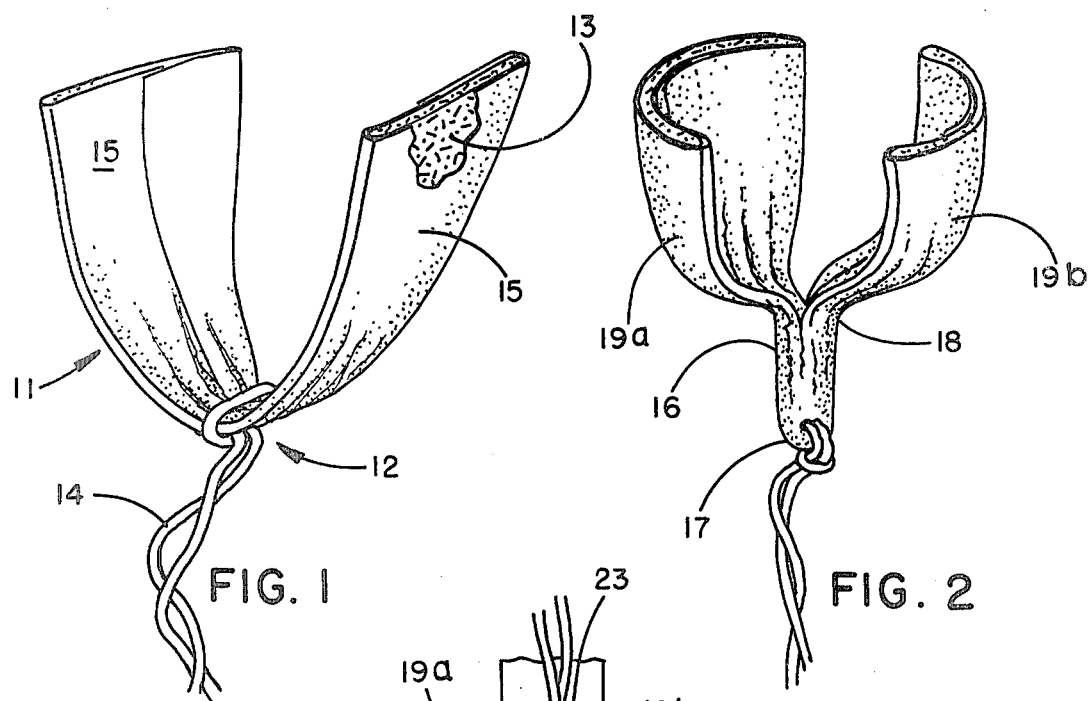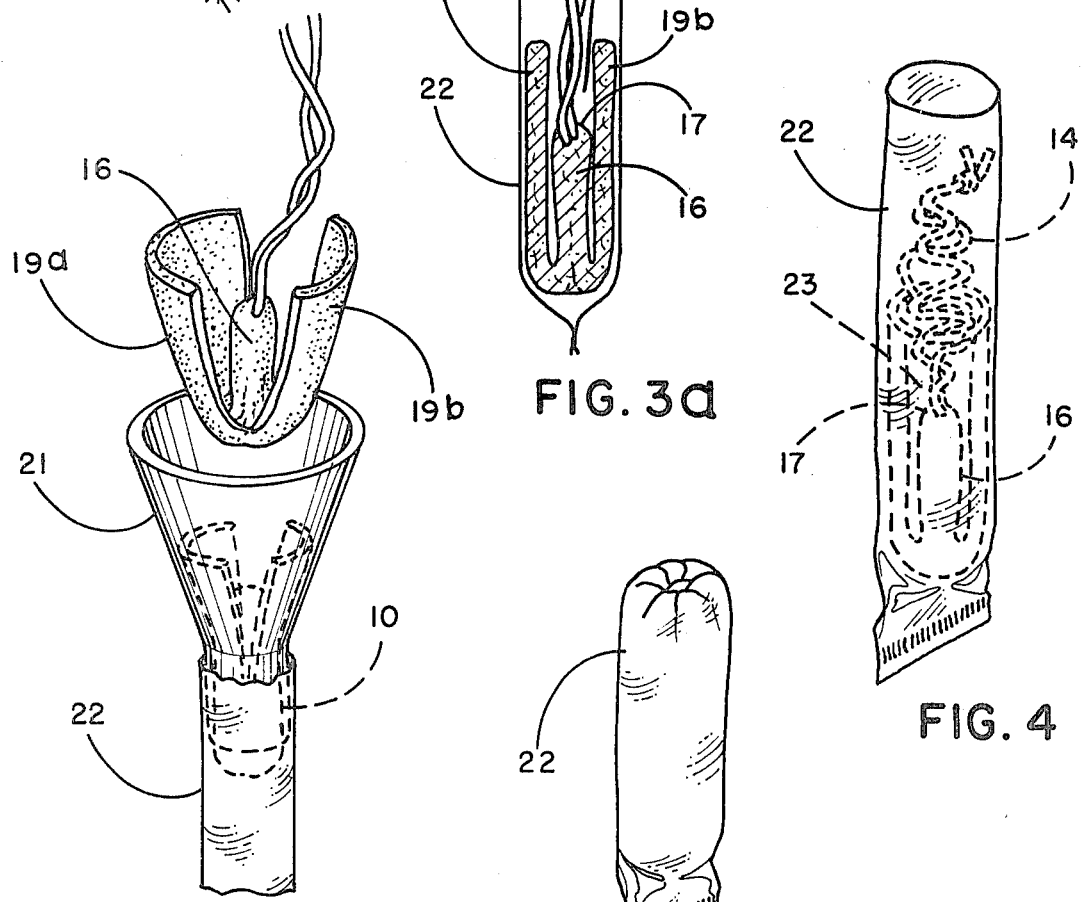

DIGITAL TAMPON

BACKGROUND OF THE INVENTION

This invention relates generally to absorbent tampons and more specifically to catamenial tampons particularly adapted for digital insertion.

Digital tampons have been on the market for many years but for a number of reasons have been much less popular than tampons which employ tube or stick-type applicatios. Since digital tampons do not require separate applicators, packaging is more compact and less conspicuous and is one of the reasons they are preferred by some tampon users.

Some of the less desirable features of digital tampons which discourage potential users include the following: (1) The small size and necessity for grasping with the fingers make it difficult to handle and insert. (2) During insertion the fingers invariably get soiled with body fluids. (3) The entire tampon is usually of highly compressed construction which does provide sufficient rigidity for insertion but inhibits rapid expansion and does not have a soft outer surface. (4) In most cases, directional deployment after insertion is usually not possible.

In the prior art, some attempts have been made to overcome these difficulties but none of the tampons incorporating such features have been successfully marketed.

Among the prior art patents related to digital tampons, U.S. Pat. Nos. 3,135,262 Kobler et al, 3,358,686 Asaka, 3,674,029 Bates et al, and 3,946,737 Kobler are typical of the many proposed arrangements designed to prevent fingers from getting soiled.

U.S. Pat. No. 4,027,673 to Poncy et al discloses a relatively non-compressible core enclosed in an elastomeric foam jacket for surface cushioning. An extension of the foam jacket provides a skirt to receive the finger of the user for digital insertion.

U.S. Pat No. 4,041,948 Flam et al employs a separate and distinct rigidifying central element in combination with a main absorptive body of softer materials. The purpose of the rigidifying central element being to provide sufficient structural support for digital insertion.

While each of these prior art digital tampons serves to alleviate some of the problems enumerated above, the prior art structures are of multi-element construction which complicates the potential for economical mass production.

In the non-digital prior art, U.S. Pat. No. 3,572,341 to Glassman shows a tampon of unitary construction in which the lower end of the tampon is highly compressed to such degree that it is adapted to retain its compressed condition at all times prior to and during use. The compressed end of Glassman is designed to be very resistant to the free flow of menstrual fluids and to provide a barrier to leakage of wastes prior to total absorption by the tampon. The concept and purpose of the Glassman disclosure is not the same as disclosed herein.

The present invention is directed to a unitary tampon which utilizes conventional materials to provide an improved tampon having internal rigidity for structural support during insertion; external conformability for comfort; protection against finger soilage; positive insertion control; and deployment and positioning capabilities after insertion. In addition, the internal rigid structure functions as a highly absorbent member for collecting and holding menstrual fluid during use.

SUMMARY OF THE INVENTION

The improved digital tampon of the present invention is of unitary construction and is made from a body of conventional absorbent material which is initially of low density but is capable of being compressed to self-sustaining form. The initial unitary body of low density absorbent material is converted into a digital tampon by having a lower portion compressed preferably in the radial direction to form a rigid rod-like element which provides a central rigidified elongated core for internal support of the tampon. The remaining upper portion of the unitary body of absorbent material is left substantially uncompressed. This relatively uncompressed portion extends from the top end of the elongated core and is draped down and around all sides of the core to a point terminating below the bottom end of the core while forming a finger-receiving pocket based at the bottom end of the core. A withdrawal cord is secured to the central core and extends from the pocket.

The tampon of the above-described structure is preferably reduced in diameter by squeezing it into a tight-fitting constraining wrap which maintains the tampon in a compact form of suitable shape and size prior to use. When using the tampon, the user first removes the wrap, the withdrawal string is then stretched out and the tip of a finger is inserted in the bottom pocket. The rigid core positively supports the tampon to permit the soft leading end to penetrate the introitus during insertion. After insertion, the inserting finger may be used to fan out the walls of the pocket in any selected direction, or peripherally, to form an immediate seal against fluid leakage or bypass.

The expression "material capable of being compressed to self-sustaining form" is meant to cover any of the conventional absorbent materials used in tampon manufacture which when compressed sufficiently will remain in rigid compressed form until the compression is released by moisture absorption. As taught in the prior art, heat, moisture, or water-soluble adhesives may be used during compression to achieve the desired self-sustaining form.

The expression "unitary construction" is meant to include a structure which, before being formed into the tampon, is a body of material having essentially the same type of composition throughout. For example, the body of material could be a substantially uniform mass of cellulosic fibers or particles such as cotton, rayon, wood pulp, fragmented cellulose sponge and the like, and mixtures thereof, enclosed in a fluid-permeable wrapper. The fibrous mass may be multilayered or homogeneous in structure. The enclosed mass could also take the form of a cylindrical tube; an elongated batt transversely folded on itself; multiple strips of material crossing at a central point and then folded upwardly; a closed-end bag, and the like. These and other variations will be shown in the drawings and described in the detailed description which follows.

BRIEF DESCRIPTION OF THE DRAWINGS

FIG. 1 is a perspective view with a surface portion cut away, of the simplest embodiment of a starting unitary absorbent body from which a first embodiment of a tampon in accordance with this invention may be fabricated.

FIG. 2 is a perspective view of the absorbent body of FIG. 1 after the lower portion has been compressed to form a self-sustaining rigid rod-like element.

FIG. 3 illustrates further processing steps which may be used to form the FIG. 1 body into a tampon while inserting it into a constricting wrap.

FIG. 3A is a sectional view of the tampon in the constricting wrap.

FIG. 4 illustrates the FIG. 1—3 tampon after insertion in a constricting wrap.

FIG. 5 shows one embodiment of the wrapped tampon of FIG. 1—3.

DETAILED DESCRIPTION OF THE INVENTION

Figure 6:
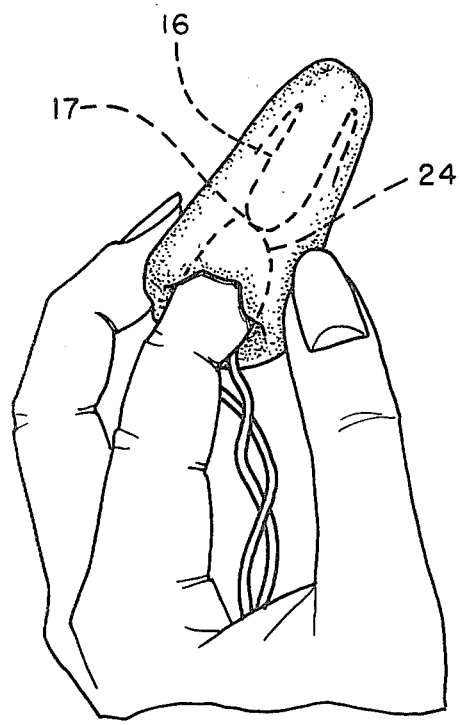
FIG. 6 is a perspective view showing the FIG. 1—3 tampon ready for insertion.

FIG. 1 is a perspective view, with a surface portion cut away, of the simplest form of a starting unitary absorbent body from which one embodiment of a tampon in accordance with this invention may be made.

The absorbent body 11 comprises a flat elongate batt of fibrous material 13 enclosed in a fluid pervious wrapper 15. As shown, the elongate batt is already partially folded transversely at about its mid-point 12 and a withdrawal cord 14 is looped around the batt at the fold.

In FIG. 2, a lower end portion of the folded batt from the fold forward is compressed, preferably in the radial direction, to an extent sufficient to provide a self-sustaining rigid rod-like element 16 having a bottom end 17 and a top end 18. In forming the tampon, the remaining upper portion of the batt comprising substantially uncompressed low density sections 19a and 19b which originate at the top end 18 of rod-like element 16 are draped around the rod-like element as shown in FIG. 3, then pressed through a conical forming means 21 as shown in the shadow outline 10 into a cylindrical retaining wrap 22. The uncompressed low density sections 19a and 19b of the thus-formed tampon are retained in substantially cylindrical shape by wrap 22.

As shown in the sectional view of FIG. 3a, the trailing low density sections 19a and 19b of the formed tampon extend to a point beyond the bottom end 17 of rod-like elment 16 to form the walls of a cylindrical finger-receiving pocket 23.

Withdrawal cord 14 is tucked into pocket 23 as shown in FIG. 4 and the open ends of wrap 22 may then be tucked into the pocket to provide the finished wrapped tampon as shown in FIG. 5.

Alternatively the open end of the wrap may also be closed by a flat heat seal, or the like similar to the closure shown at its bottom end.

Figure 7:
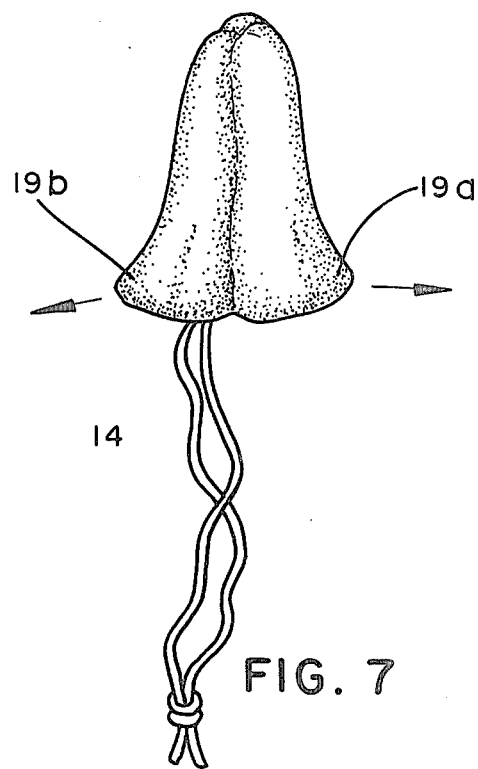
FIG. 7 illustrates how the FIG. 1—3 tampon may be deployed by widening the pocket sides with the finger after insertion.

FIGS. 6 through 10 illustrate how the tampon of FIGS. 1-5 may be inserted. After the wrap is removed, the tip of one finger is inserted in the finger-receiving pocket so that the forward end 24 of the finger rests against the bottom end 17 of rod-like element 16. The tampon is thereby coupled with the finger for positive control and guidance before and during insertion. Uncompressed sections 19a and 19b which form the wall of the pocket also serve as finger protectors, and additionally shield the fingernail of the inserting finger from skin contact, while preventing exudate from soiling the inserting finger during insertion. After insertion, the inserting finger may be manipulated, if desired, to spread the free ends of the pocket walls as shown in FIG. 7 to provide an immediate seal against side leakage.

Figure 8:
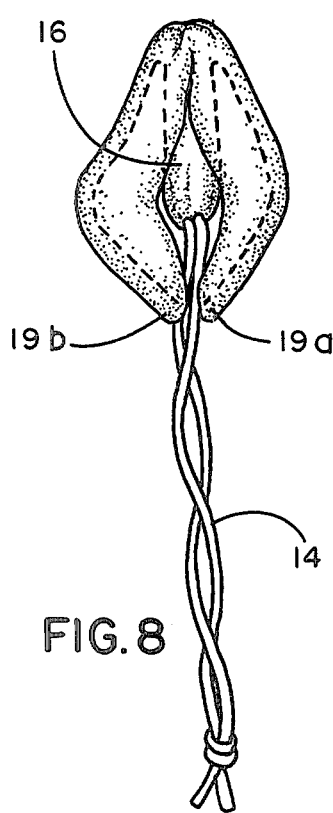
FIG. 8 indicates the shape the FIG. 1—3 tampon usually assumes after insertion.
Figure 9:
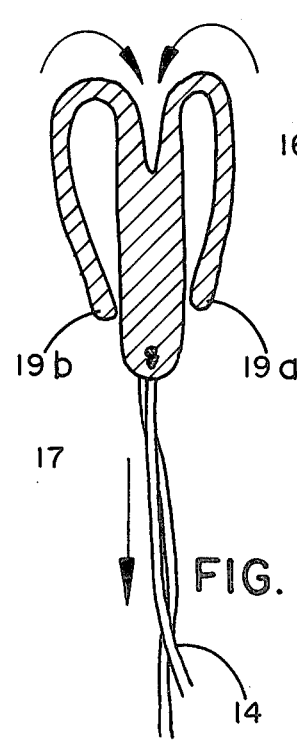
FIG. 9 is a longitudinal section illustrating how the FIG. 1-3 tampon begins to evert as it is being withdrawn.
Figure 10:
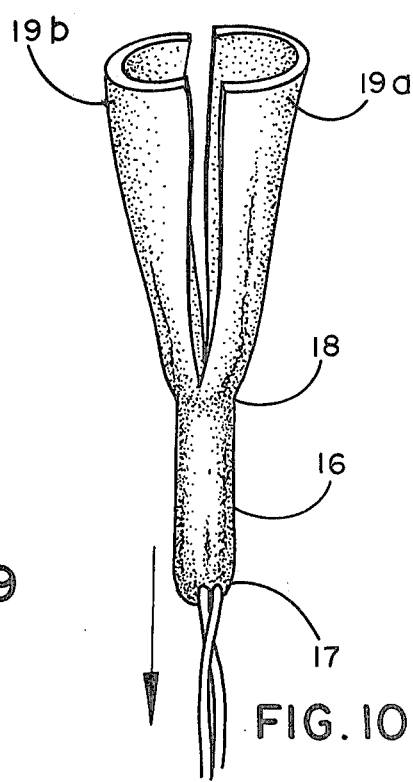
FIG. 10 shows the everted FIG. 1—3 tampon after withdrawal.

After the finger has been removed leaving the tampon in place, vaginal pressure usually tends to press against the tampon and cause the lower ends of sections 19a and 19b to assume the shape shown in FIG. 8. In circumstances under which the tampon absorbs considerable exudate, this shape will be substantially retained during removal since the exudate reduces frictional contact with the vaginal wall and serves as a lubricant to ease removal. However, during times of light flow, or in the event of early removal, when the exterior surfaces are relatively dry, the exterior surfaces tend to be in stronger frictional engagement with the vaginal wall during removal and while being withdrawn the tampon will tend to evert and assume the inverted shape shown in FIG. 10.

Figure 11:
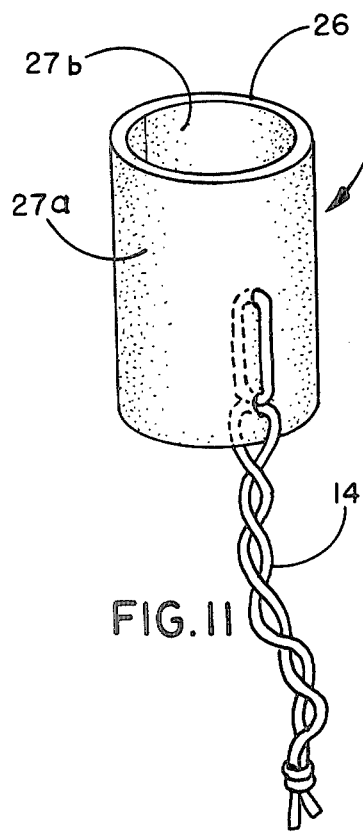
FIG. 11 is a perspective view of a cylindrical form of a starting absorbent body from which another embodiment of the tampon may be made.

FIG. 11 shows another form of a unitary absorbent body from which the tampon may be formed. In this case the compressible absorbent material 26 is enclosed in an outer pervious wrapper 27a and an inner pervious wrapper 27b and formed in a cylindrical tube 25 with a withdrawal string 14 secured thereto. Various forms of cord securement other than that shown may, of course, be used.

Figure 12:
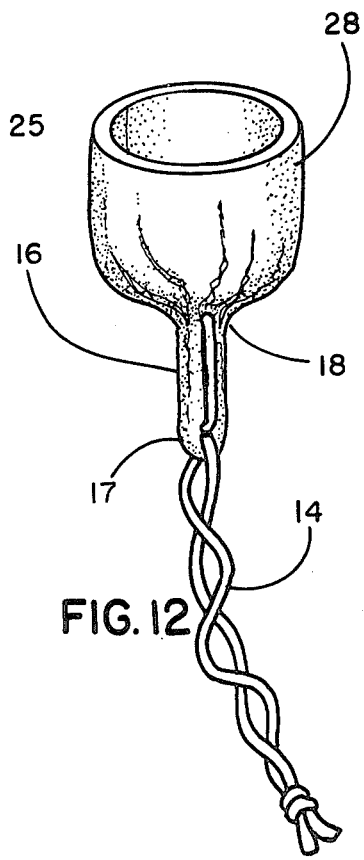
FIG. 12 is similar to FIG. 2 showing the absorbent body of FIG. 11 after the lower portion is compressed.
Figure 13:
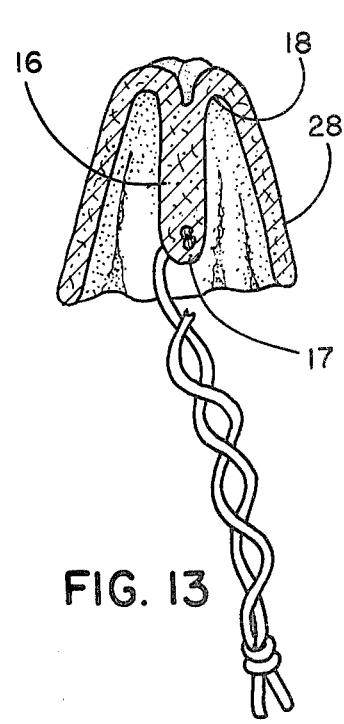
FIG. 13 is longitudinal cross section showing the tampon body of FIG. 12 with the upper end draped over the compressed lower end.
Figure 14:
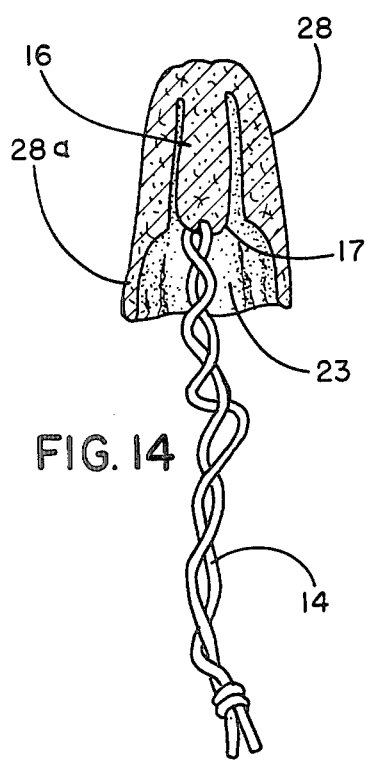
FIG. 14 is a sectional view showing the tampon of FIG. 13 in finished form.

FIG. 12 shows the lower portion of starting cylindrical absorbent body 25 compressed to self-sustaining form to provide rigid rod-like element 16 having a bottom end 17 and a top end 18. The remaining uncompressed low density upper portion 28 of the tube-like cylindrical body is first inverted as shown in the sectional view of FIG. 13, then pressed into a cylindrical retaining wrap as previously described to provide a finished tampon in the same manner as shown in sectional view of FIG. 3a. The resulting tampon has a core comprised of the high density rigid rod-like element 16 surrounded by the substantially uncompressed low density upper portion 28 of the starting cylinder. This low density upper portion is draped down around element 16 and extends beyond the bottom end 17 of the rod-like element 16 to provide the walls of the finger-receiving pocket 23. In a slightly modified form, the lower portion of the walls of pocket 23 may be highly compressed as shown at 28a to make a firmer pocket.

Figure 15:
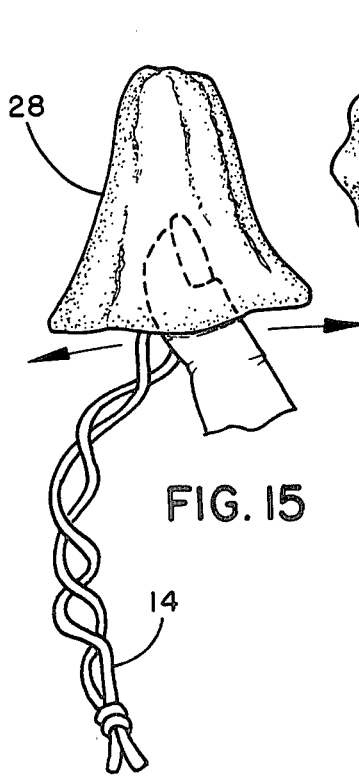
FIG. 15 illustrates how the FIG. 14 tampon may be finger deployed after insertion.

FIG. 15 shows how the walls of the pocket may be deployed by the finger after insertion.

Figure 16:
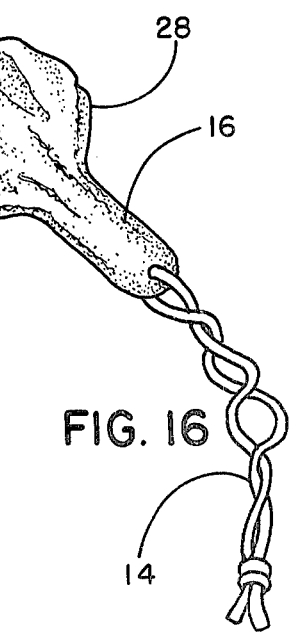
FIG. 16 shows the everted FIG. 14 tampon after withdrawal.

FIG. 16 illustrates how the FIG. 15 form of the inserted tampon will become inverted in the event of early removal.

Figure 17:
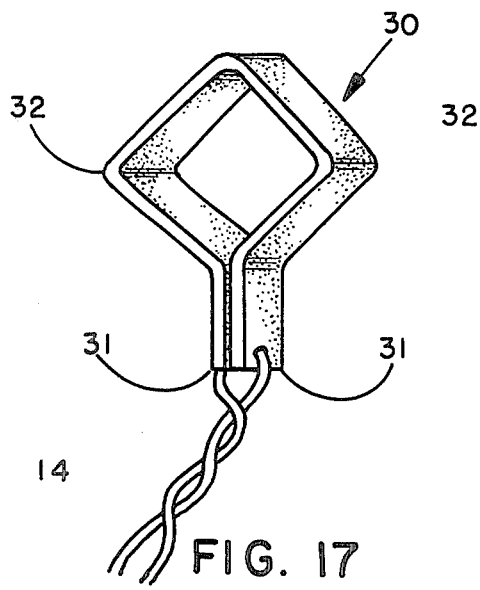
FIG. 17 is a perspective view of another form of a starting absorbent body.
Figure 18:
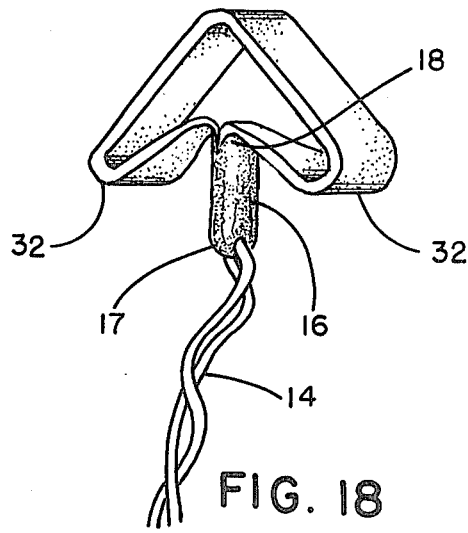
FIG. 18 shows the absorbent body of FIG. 17 after compression of the lower end and preliminary forming of the upper uncompressed end.

FIG. 17 and 18 show another embodiment of a tampon of this invention.

In this embodiment the starting unitary absorbent body 30 is in the form of an elongate batt shaped initially like an inverted U with the withdrawal cord 14 securing the free ends 31 of the U together to form a closed loop. Stated another way the unitary absorbent body 30 comprises an elongate strip transversely folded in half with the withdrawal cord securing together the free ends of the strip which are disposed opposite the fold.

As shown in FIG. 18 the lower portion of the closed loop, formed by the tied-together free ends of the strip is compressed sufficiently to form the rigid rod-like element 16 with a bottom end 17 and top end 18.

The upper closed end of the loop is then flattened to form opposing hinge areas 32, and the flattened loop is then folded downward to enclose rod-like element 16 and provide a finger-receiving pocket as previously described for the earlier embodiments. In this embodiment the hinged fold line forms the free lower end of the pocket wall.

Figure 19:
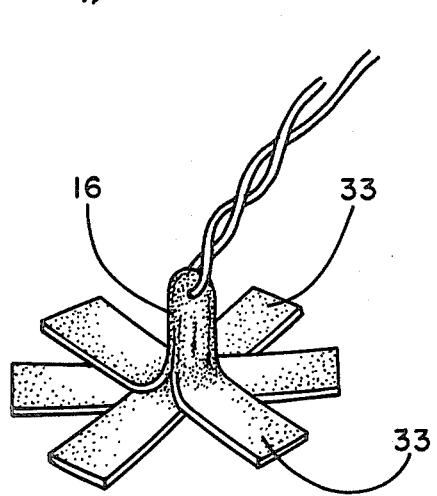
FIG. 19 is a perspective view of the bottom end of a partially formed tampon body after compressing the bottom end of a unitary body of absorbent material comprised of multiple crossed strips.

FIG. 19 shows another embodiment in which the unitary absorbent body comprises a multiplicity of intersecting strips 33. The lower portion of the body centers at the intersection of the strips and it is this portion which is compressed to form rod-like element 16.

The additional forming of this embodiment into a finished tampon with a finger-receiving pocket is again the same as previously described. The strips 33 being draped around the rod-like element 16 to form the pocket.

Figure 20:
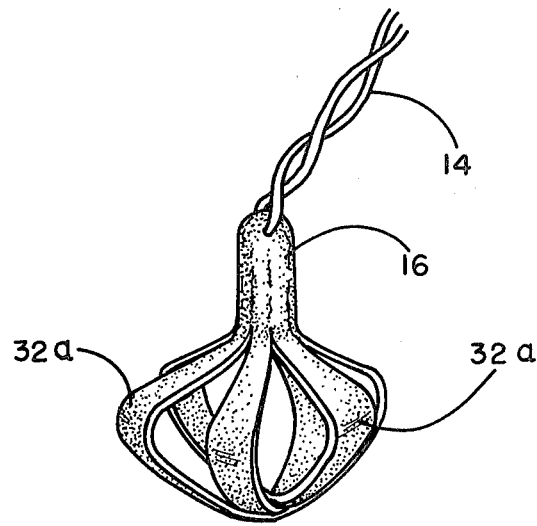
FIG. 20 is a perspective view of a partially formed tampon body similar to the body of FIG. 17-18, but made of multiple loops.

In FIG. 20, the unitary absorbent body comprises a multiplicity of closed loops with fold lines at 32a similar to what is shown in FIGS. 17-18. The tampon is formed and shaped in the same way as described with respect to FIGS. 17-18.

Figure 21:
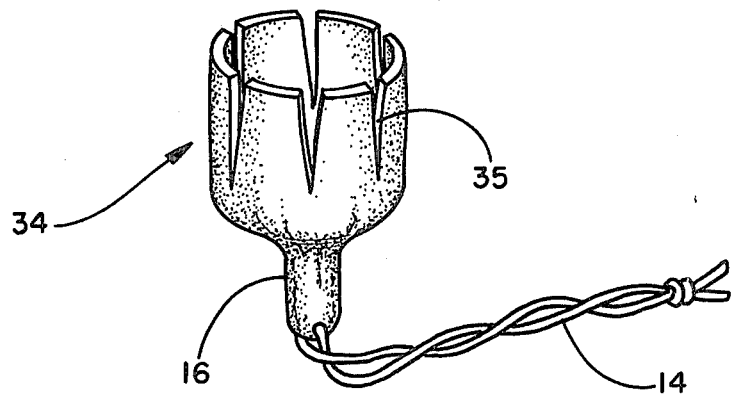
FIG. 21 is a perspective view of a partially formed tampon body of the cylindrical type shown in FIGS. 11-16 but having the top edges slit before draping.

FIG. 21 shows still another embodiment in which the upper end 34 of a cylindrical tube similar to that shown in FIGS. 11-16 has the upper end of the uncompressed portion provided with spaced longitudinal slits 35 before the tampon is formed.

Figure 22:
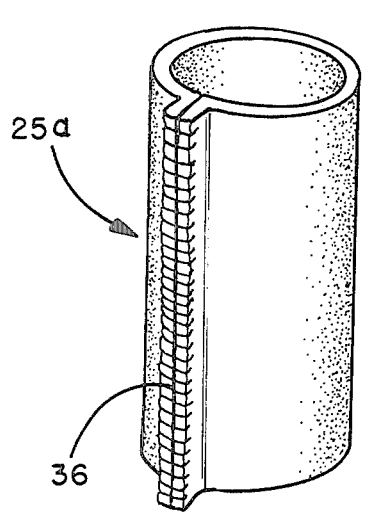
FIG. 22 is a perspective view of another cylindrical embodiment of a starting unitary body of absorbent material.
Figure 23:
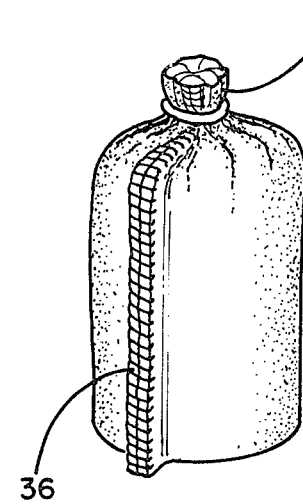
FIG. 23 shows the unitary body of FIG. 22 with the top end closed.
Figure 24:
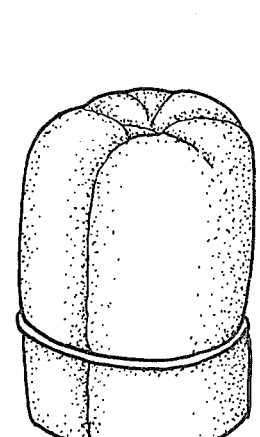
FIG. 24 shows the closed-end body of FIG. 23 after being turned inside out and with a withdrawal cord in place.

FIG. 22 is also a variation of the FIGS. 11-16 embodiment in which the tube 25a is formed by using a rectangular blank and securing two edges together as at 36, by stitching or by adhesive. The thus formed tube 25a then has its upper end closed as shown at 37 in FIG. 23 and is then turned inside-out as shown in FIG. 24 to form a bag with the closed end at the top.

Figure 25:
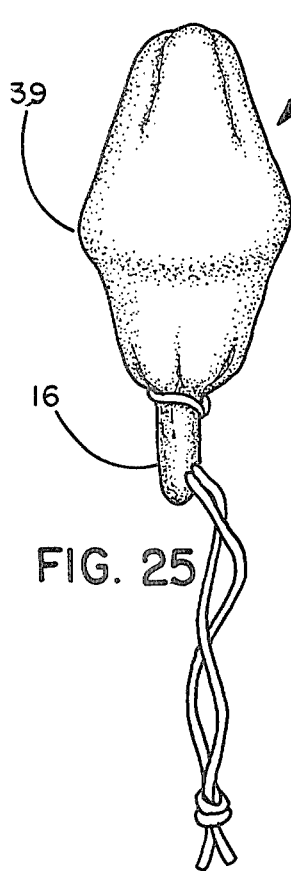
FIG. 25 shows the partially formed tampon of FIG. 24 after compression of the lower end.

Withdrawal cord 14 is then secured to the lower portion which is compressed to form rod-like element 16, as shown in FIG. 25.

Figure 26:
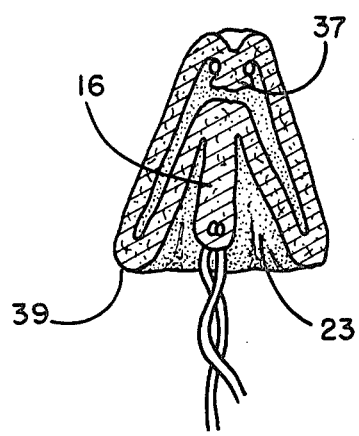
FIG. 26 is a longitudinal cross section showing the tampon body of FIG. 25 in the process of having its top end folded down over the central rod.
Figure 27:
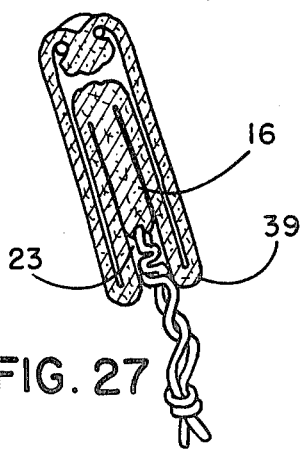
FIG. 27 is a longitudinal cross section of the FIG. 26 tampon in finished form.

The bulbous uncompressed upper portion 38 is then squashed down mushroom style resulting in a circumferential hinged portion 39 near the center of the bulbous portion, which when draped down over element 16 becomes the finger-receiving pocket 23 as shown in the sectional views of FIGS. 26 and 27.

Figure 28:
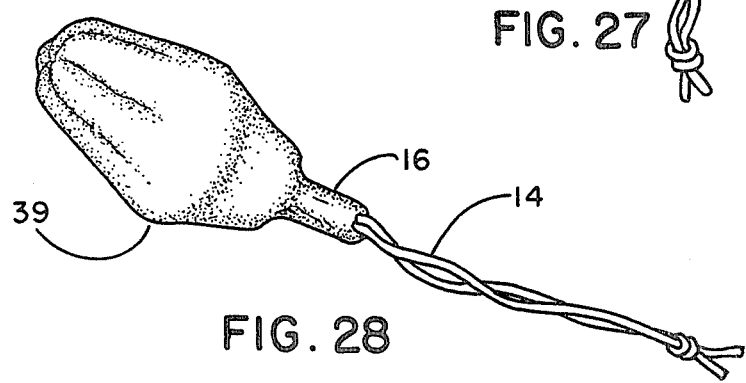
FIG. 28 is a perspective view of the FIG. 27 tampon after it has been everted during withdrawal.

FIG. 28 shows the everted form this embodiment of the tampon may take upon withdrawal.

While the tampon of this invention is intended primarily for digital insertion it is easily adapted to the use of a finger extension in the event deeper insertion is desired.

Figures 29, 30:
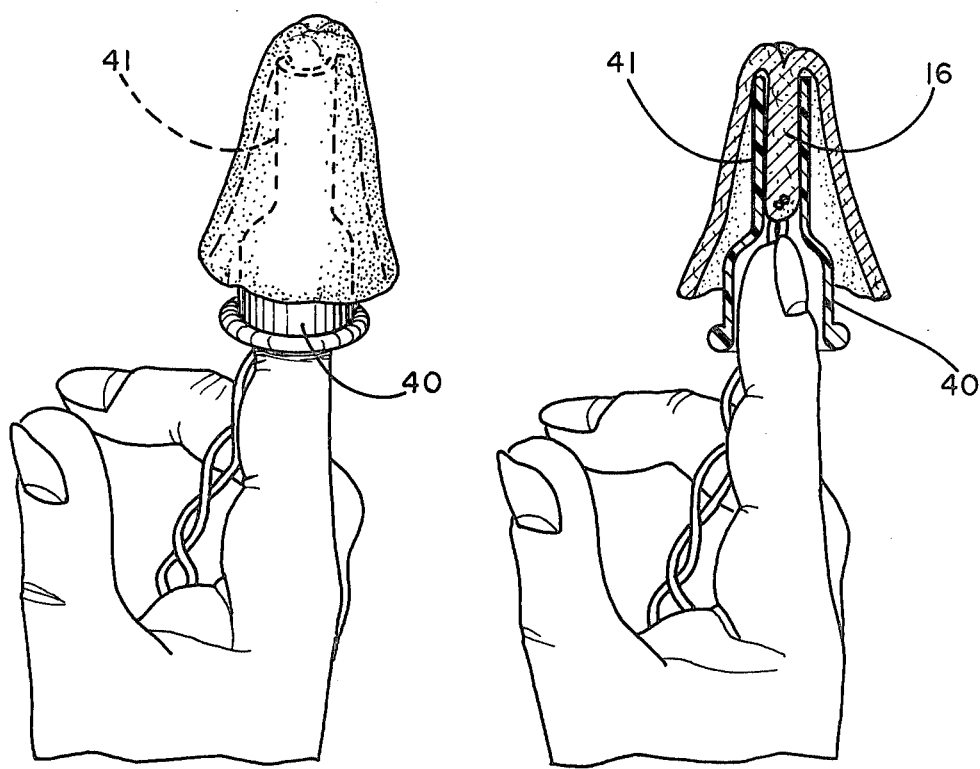
FIG. 29 is a perspective view showing the utilization of a finger extension device with a tampon of this invention.
FIG. 30 is a longitudinal cross section of the tampon portion of FIG. 29.

FIGS. 29 and 30 illustrate one embodiment of such finger extension as adapted to the tampon. The extension may be in the shape of a plastic thimble 40 with a hollow extension 41. As shown, the hollow extension 41 fits around rod-like element 16. The finger fits in thimble 40 and the tampon may then be inserted in the usual manner.

The tampon may also be used in tube inserters of the conventional type.

While a number of embodiments of the tampon of this invention have been described and illustrated it is understood that there are many other variations which may be used while still employing the principles and methods described herein.

There are also many absorbent materials which may be used to form the unitary absorbent body from which the tampon of this invention may be made. One specific formulation which is particularly desirable because of the availability of materials and low cost comprises a mixture of cotton fibers and rayon fibers which are formed into a soft batt by airlaying or carding and enclosed in a bonded carded web. Bonded carded webs are well known for this use and generally comprise rayon fibers bonded by saturation, printing or coating with a polyvinyl acetate. Non-woven scrim construction and spunbonded webs may also be used for the batt-enclosing wrapper. Ranges of fiber mixtures of from about 70% to 50% cotton and about 30% to 50% rayon have been found satisfactory.

In addition to the cotton-rayon fiber mixture, super-absorbent fibers or powders may also be added. A particularly useful mixture has been found to be about 50% cotton, 40% rayon and 10% super-absorbent fibers. A range of about 3% to 10% super-absorbant materials have been found useful. Rayon polyacrylate fibers may also be used, and various sponge-like absorbent materials such as cellulose sponge, and cross-linked polyurethane or polyester foams.

In any event the unitary absorbent body incorporating any of these materials must be capable of being compressed to a self-sustaining form which is releasable when contacted by body exudates during use.

The substantially uncompressed outer structure in the unitary tampon of this invention has several desirable attributes. First, because it is of low density and soft, it is comfortable during insertion and while worn. Second, it conforms readily to vaginal pressure to minimize side wall leakage. Third, it serves to wipe the walls clean during insertion. Fourth, it provides high absorbent capacity immediately upon insertion and does not need to be contacted by exudate to provide initial high capacity.

The unitary compressed element forming the supporting central core also provides desirable attributes. First, it supports the soft outer shell during insertion. This was formerly supplied in prior art tampons by separate and distinct rigid means and not by a unitary part of the absorbent body. Second, because the rigid element is an integral part of the absorbent body, absorbed fluids migrate into the central area more readily. Third, because the rigid element is compressed, it has smaller capillaries which draw fluid from the lower density outer portions.

Since the compression of the central rod-like element is preferably radial, it expands radially as it absorbs fluid to help press the exterior of the tampon outwardly against the vaginal walls and maintain good contact therewith.

What is claimed is:

1. A tampon of unitary construction comprised of a compressible absorbent material a lower portion of said material being compressed to provide a rigid insertion means for finger contact and support of soft outer shell during insertion, the remaining upper portion of said material being relatively uncompressed and being draped downwardly from the top of said insertion means to surround said insertion means and extend past the lower terminus of said insertion means to provide a downwardly-facing finger-receiving pocket, and a withdrawal string secured to and extending from said insertion means.

2. A digital tampon comprising a generally elongate absorbent body of unitary construction, said body being comprised of a compressible absorbent material; a lower portion of said absorbent body having been radially compressed to provide a rigid centrally disposed insertion means for finger contact and support of soft outer shell during insertion, having a top end and a bottom end; the remaining upper portion of said absorbent body being relatively uncompressed with said upper portion overhanging the top end of said insertion means to substantially surround said insertion means and extend below the bottom end of said insertion means to provide a small downward facing finger-receiving pocket based at the bottom end of said insertion means; and a withdrawal cord, one end of which is secured to at least the bottom end of said insertion means.

3. In a tampon adapted for digital insertion and which comprises a central rigidified core member surrounded by an outer absorptive and fluid-permeable member and is further provided with a withdrawal cord and a finger-receiving pocket at the bottom end to facilitate insertion; the improvement wherein the tampon comprises a unitary body of compressible absorbent material; in which the central core member is a rigid insertion means for finger contact and support of soft outer shell during insertion comprised of a lower portion of said unitary body compressed to self-sustaining condition; in which the outer member is comprised of the remaining upper portion of said unitary body in substantially uncompressed condition and integral with said insertion means; in which said outer members extends out from the top end of said insertion means, hangs downward around on all sides of said insertion means, and terminates beyond the bottom end of said insertion means to form a finger-receiving pocket based at said bottom end; and in which said withdrawal cord is secured to said insertion means.

4. The tampon of claim 3 wherein said unitary body comprises an elongate strip transversely folded substantially in half with said lower portion originating at the fold 5. The tampon of claim 4 wherein said upper portion comprises the free ends of said folded strip folded downwardly over said central core and forming said finger-receiving pocket.

6. The tampon of claim 3 wherein said unitary body is in the form of a cylindrical tube.

7. The tampon of claim 6 wherein the upper portion of said tube has a multiplicity of spaced longitudinal slits.

8. The tampon of claim 3 wherein said unitary body comprises an elongate strip transversely folded in half with the free ends secured together by the withdrawal cord and with said lower portion originating at said secured together free ends.

9. The tampon of claim 8 wherein said upper portion extends to the closed end of said folded strip, and the sides of said upper portion are hinged outweardly and draped downwardly over said central core and forming the walls of said finger-receiving pocket.

10. The tampon of claim 3 wherein said unitary body comprises a multiplicity of strips crossing each other at their approximate mid-points, said crossed strips being folded transversely at said mid-point with said lower portion originating at said mid-point fold.

11. The tampon of claim 10 wherein said upper portion comprises the free ends of said crossed strips draped downwardly over said central core and forming said finger-receiving pocket.

12. The tampon of claim 3 wherein said unitary body comprises a multiplicity of strips crossing each other at their approximate mid-points, said crossed strips being folded transversely at said mid-point and with the free ends of said strips being secured together by the withdrawal cord and with said lower portion originating at said secured together free ends.

13. The tampon of claim 12 wherein said upper portion extends to the crossover area of said strips, and the sides of the upper portion of said strips are hinged outwardly and draped downwardly over said central core and form said finger-receiving pocket.

14. The tampon of claim 3 wherein said unitary absorbent body comprises an elongate bag closed on one end and the opposite end of said bag is in the lower portion of said body which is compressed to form said central core.

15. The tampon of claim 14 wherein the side walls of said closed end of the bag are collapsed outwardly and mushroomed down around said core and form said finger-receiving pocket.

* * * * *